United States Patent [19]

Garner et al.

[11] 4,054,718
[45] Oct. 18, 1977

[54] HEAT-SENSITIVE RECORDING MATERIAL CONTAINING A MALACHITE GREEN COLOR FORMER

[75] Inventors: Robert Garner, Bury, England; Jean Claude Petitpierre, Kaiseraugst, Switzerland

[73] Assignee: Ciba-Geigy Corporation, Ardsley, N.Y.

[21] Appl. No.: 651,108

[22] Filed: Jan. 21, 1976

[30] Foreign Application Priority Data

Jan. 27, 1975 Switzerland ............................ 951/75

[51] Int. Cl.² .......................... B32B 29/04; B32B 9/06
[52] U.S. Cl. ..................................... 428/454; 428/144; 428/323; 428/488; 428/535; 428/538; 428/477; 427/150; 427/151; 427/261; 282/27.5; 428/496; 428/481; 428/512; 428/514
[58] Field of Search ............... 428/411, 488, 535, 538, 428/144, 323, 454; 427/150, 151, 261

[56] References Cited

FOREIGN PATENT DOCUMENTS 1,135,540 12/1968 United Kingdom
852,131 10/1960 United Kingdom

OTHER PUBLICATIONS

Ginzburg et al., "Condensation Products et al.," J. Gen. Chem. USSR, 23, 1953, pp. 1103–1106.

*Primary Examiner*—P. C. Ives
*Attorney, Agent, or Firm*—Karl F. Jorda; Edward McC. Roberts; Prabodh I. Almaula

[57] ABSTRACT

A heat-sensitive recording material which contains as color former at least one compound of the general formula

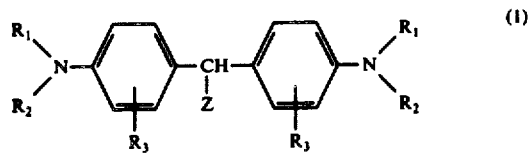

wherein $R_1$ and $R_2$, which can be the same or different, represent hydrogen, alkyl of at most 12 carbon atoms which is unsubstituted or substituted by cyano or halogen, alkoxyalkyl of 2 to 8 carbon atoms, benzyl or phenyl, $R_3$ represents hydrogen, halogen, nitro, alkyl of 1 to 4 carbon atoms or alkoxy of 1 to 4 carbon atoms, and Z represents alkenyl of at most 12 carbon atoms, unsubstituted or ring-substituted aralkyl or aralkenyl, or represents the radical of a reactive organic methylene compound or of a heterocyclic compound which does not contain active methylene groups.

14 Claims, No Drawings

HEAT-SENSITIVE RECORDING MATERIAL CONTAINING A MALACHITE GREEN COLOR FORMER

The present invention provides a heat-sensitive recording material which contains as colour former a compound of the general formula

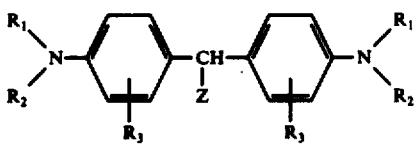

(1)

wherein $R_1$ and $R_2$, which can be the same or different, represent hydrogen, alkyl of at most 12 carbon atoms which is unsubstituted or substituted by cyano or halogen, alkoxyalkyl of 2 to 8 carbon atoms, benzyl or phenyl, $R_3$ represents hydrogen, halogen, nitro, alkyl of 1 to 4 carbon atoms or alkoxy of 1 to 4 carbon atoms, and Z represents alkenyl of at most 12 carbon atoms, unsubstituted or ring-substituted aralkyl or aralkenyl, or represents the radical of a reactive organic methylene compound or of a heterocyclic compound which does not contain active methylene groups.

Alkyl groups represented by the substituents $R_1$ and $R_2$ can be branched or preferably straight-chain. Examples of such alkyl radicals are methyl, ethyl, n-propyl, isopropyl, n-butyl, sec. butyl, n-hexyl, n-octyl or n-dodecyl.

Substituted alkyl radicals $R_1$ and $R_2$ are primarily haloalkyl and cyanoalkyl, each of 2 to 4 carbon atoms, for example β-chloroethyl and β-cyanoethyl.

Alkoxyalkyl groups represented by $R_1$ and $R_2$ can contain 1 to 4 carbon atoms in each of the alkyl moieties; preferred alkoxyalkyl radicals are β-methoxyethyl and β-ethoxyethyl.

Alkyl represented by $R_3$ is preferably methyl and alkoxy represented by $R_3$ is preferably methoxy and ethoxy.

Alkenyl represented by Z is, for example, allyl, 2-methallyl, 2-ethylallyl, 2-butenyl or octenyl.

Aralkenyl or aralkyl represented by Z can be styryl, phenylethyl or preferably benzyl. Where the benzene nucleus of these araliphatic radicals is substituted, it can contain, for example, halogen, nitro, alkyl of 1 to 4 carbon atoms or alkoxy of 1 to 4 carbon atoms.

Where Z represents the radical of an organic compound with an active methylene group, it is attached to the bis-arylmethane radical through the methylene group. The methylene compounds can be aliphatic, cycloaliphatic or heterocyclic. The aliphatic compounds are, for example, compounds of the formula X—CH$_2$—Y, wherein X represents an electrophilic group and Y represents an inert, i.e. inactive, organic group, for example an alkyl group or a phenyl group which is unsubstituted or substituted by alkyl or alkoxy of 1 to 4 carbon atoms or also represents an electrophilic group; the electrophilic groups represented by X and Y can be the same or different. Examples of possible electrophilic groups are: nitro, cyano, acyl groups of 2 to 12 carbon atoms, for example alkanoyl or benzoyl, carboxy ester groups, such as carbalkoxy groups of 2 to 5 carbon atoms or substituted or unsubstituted carbo- phenoxy groups, the carboxy amide or sulphonamide group, N-monosubstituted or N,N-disubstituted carbamoyl or sulphamoyl groups with a substituted or unsubstituted phenyl, benzyl and/or alkyl group of 1 to 4 carbon atoms, the N,N-substituents of these amide groups, together with the nitrogen atom to which they are attached, also being able to form a 5- or 6-membered heterocyclic ring; and also negatively substituted aromatic radicals, for example nitrophenyl radicals, in particular o- and/or p-nitrophenyl or aromatic heterocyclic rings which contain tertiary nitrogen. Malonic dinitrile, benzyl cyanide, cyanoacetic acid esters and arylamides may be cited as examples thereof. The methylene compounds which contain a reactive ketomethylene group merit particular mention, in which connection both those compounds that contain the group in open chain and those in which the group forms the constituent of a carbocyclic or heterocyclic ring are suitable.

The following compounds may be cited as examples of those belonging to the class of open ketomethylene compounds:

aliphatic 1,3-diketones, for example acetyl acetone, malonic $C_1$-$C_4$-alkyl and phenyl esters and amides, acylacetic $C_1$-$C_4$-alkyl and phenyl esters and amides whose benzene nuclei are unsubstituted or substituted by methyl, methoxy, ethoxy, cyano, halogen or nitro, for example acetoacetic anilide, acetoacetic chloroanilides, acetoacetic toluidides, acetoacetic xylidides, acetoacetic anisidides, acetoacetic phenetitides or benzoylacetic anilides.

Cyclic, i.e. cycloaliphatic or heterocyclic, ketomethylene compounds are, for example, 1,3-indandione, 5,5-dimethyl-1,3-dioxo-cyclohexane, thiazolones, 2,4-dioxo-tetrahydrofurans, 2,4-dioxo-pyrrolidines, 5-pyrazolones, 3,5-dioxo-pyrazolidines, oxindoles, pyronones, 4-hydroxy-2-quinolones, hydroxypyridones, hydantoins, dihydrouracils, 4,6-dioxo-pyrimidines and barbituric acids. Preferred compounds, however, are bis-aryl-leucomethylene dyes of formula (1), in which Z represents the radical of a 1-aryl-pyrazolone which is bound in 4-position, in particular of a 1-aryl-5-pyrazolone, preferably 1-phenyl-5-pyrazolone, which can be further substituted, for example in 3-position, by alkyl of 1 to 4 carbon atoms, for example methyl, for example 1-(2'-, 3'- or 4'-chlorophenyl)-3-methyl-5-pyrazolone, 1-(2'-, 3'- or 4'-methylphenyl)-3-methyl-5-pyrazolone, 1-(2'-, 3'- or 4'-methoxyphenyl)-3-methyl-5-pyrazolone or, in particular, 1-phenyl-3-methyl-5-pyrazolone.

As a heterocyclic radical which does not contain methylene groups Z represents primarily a 5- or 6-membered heterocyclic ring system of aromatic character which contains preferably oxygen, sulphur or nitrogen. Examples of heterocyclic rings are: thienyl, furyl, pyrrolyl, pyrazolyl, triazolyl, pyridyl, thiazinyl or oxazinyl radicals. Z can also represent a polynuclear heterocyclic ring system. This preferably contains a fused benzene or naphthalene ring, for example a substituted or unsubstituted benzothiophene, indole, indazole, benzothiazole, benzotriazole, naphthotriazole, quinoline, carbazole, phenothiazine or phenoxazine radical. The monouclear or polynuclear heterocyclic radicals can contain substituents of the kind referred to above, in particular halogen, cyano, nitro, alkyl of 1 to 8 carbon atoms, alkoxy of 1 to 4 carbon atoms, acyl of 1 to 8 carbon atoms or phenyl.

The preferred heterocyclic radicals which do not contain methylene groups represented by Z are the 3-indolyl radicals which are unsubstituted or substituted by halogen, cyano, nitro, alkyl of 1 to 8 carbon atoms, alkoxy of 1 to 4 carbon atoms, acyl of 2 to 4 carbon atoms, benzyl or phenyl, in particular 1-($C_1$-$C_8$-alkyl)- or 1-benzyl-2-methyl-3-indolyl. Examples of 3-indolyl radicals are 3-indolyl, 1-acetyl-3-indolyl, 1-ethyl-2-methyl-3-indolyl, 1-benzyl-2-methyl-3-indolyl and 1-n-octyl-2-methyl-3-indolyl.

Halogen atoms in connection with the above substituents are, for example, fluorine, bromine or preferably chlorine.

Important compounds of the bis-aryl-leucomethylene dyes of formula (1) have the general formula

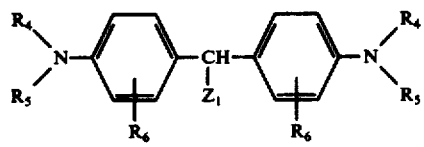
(2)

wherein
each of $R_4$ and $R_5$ independently represents hydrogen, alkyl of 1 to 4 carbon atoms or benzyl,
$R_6$ represents hydrogen, methyl, methoxy or chlorine,
$Z_1$ represents an indolyl radical which is unsubstituted or substituted by alkyl of 1 to 8 carbon atoms, alkoxy of 1 to 4 carbon atoms, alkanoyl of 2 to 4 carbon atoms, benzyl or phenyl, a 5-amino-pyrazole radical, or represents the radical of an open or cyclic ketomethylene compound, in particular of a 1-aryl-5-pyrazolone compound.

Particularly useful colour formers are compounds of the general formula

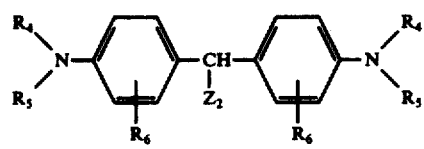
(3)

wherein $R_4$, $R_5$ and $R_6$ are as defined in formula (2), and $Z_2$ represents 1-($C_1$-$C_8$-alkyl)-2-methyl-3-indolyl, 1-benzyl-2-methyl-3-indolyl, 1-aryl-3-methyl-5-pyrazolon-4-yl, 1-aryl-3-methyl-5-amino-pyrazol-4-yl or the radical of an open or cyclic 1,3-diketone or of an acylacetic anilide which is bound through the methylene group.

The radical of an open 1,3-diketone or of an acylacetic anilide which is bound through the methylene group and represented by $Z_2$ preferably has the formula

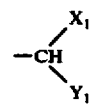
(3.1)

wherein each of $X_1$ and $Y_1$ independently represents acyl of 2 to 8 carbon atoms, preferably acetyl or benzoyl, or the group of formula

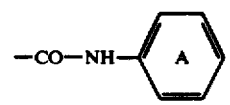
(3.2)

wherein the benzene ring A can be substituted by methyl, methoxy, halogen or nitro. $X_1$ is preferably acetyl or benzoyl and $Y_1$ is preferably acetyl or the group of formula (3.2).

As the radical of a cyclic 1,3-diketone, $Z_2$ preferably represents a 5,5-di-$C_1$-$C_8$-alkyl-1,3-dioxo-cyclohexyl radical, a 1-$C_1$-$C_4$-alkyl-4-hydroxy-2-quinolonyl radical or the radical of a 6-hydroxy-3-cyano- or -carbonamido-4-$C_1$-$C_4$-alkyl-2-pyridone, which can be substituted in 1-position by alkyl of 1 to 4 carbon atoms.

Preferred compounds of formula (3) are those in which both $R_4$ and $R_5$ are methyl or ethyl, $R_6$ represents hydrogen and $Z_2$ represents 1-methyl-2-methyl-indol-3-yl, 1-ethyl-2-methyl-indol-3-yl, 1-benzyl-2-methyl-indol-3-yl, 1-phenyl-3-methyl-5-pyrazolon-4-yl, 1-chlorophenyl-3-methyl-5-pyrazolon-4-yl, 1-phenyl-3-methyl-5-amino-pyrazol-4-yl, acetylacetonyl, 5,5-dimethyl-1,3-dioxo-cyclohex-2-yl, 1-methyl-4-hydroxy-2-quinolon-3-yl or the radical of acetoacetic anilide of formula

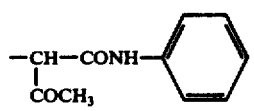
(3.3)

which is bound through the methylene group.

The compounds of formulae (1) to (3) are in part known, for example from J.Gen.Chem.U.S.S.R., 23, 1103-1106 (1953), yet constitute a new class of colour formers. They can be obtained by known processes. One process for obtaining the compounds of formula (1), wherein Z represents a substituted or unsubstituted indolyl radical or the radical of a reactive methylene compound, comprises reacting a carbinol or carbinol ether compound of formula

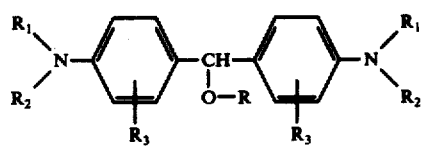
(4)

wherein R represents hydrogen or alkyl of 1 to 4 carbon atoms, for example methyl, and $R_1$, $R_2$ and $R_3$ are as defined hereinbefore, with a substituted or unsubstituted indole compound or with an organic compound with an active methylene group.

The reaction takes place advantageously in the presence of an alcohol, preferably methanol, and at room temperature.

Compounds of formula (1), in which Z represents an alkenyl, aralkenyl or aralkyl radical as defined herein or a heterocyclic radical, can be obtained by reacting two moles of an amino-substituted benzene compound of formula

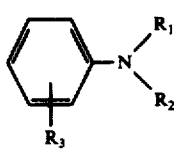
(5)

with 1 mole of an aldehyde of formula

Z — CHO (6)

wherein $R_1$, $R_2$ and $R_3$ are as defined hereinbefore and Z represents the alkenyl, aralkenyl, aralkyl or heterocyclic radical indicated for formula (1).

The compounds of formulae (1) to (3) are normally colourless or at most faintly coloured. When these colour formers are brought into contact with an acid developer, i.e. an electron acceptor, they produce violet to green colours of excellent light fastness. They are therefore also very useful when mixed with other known colour formers, for example crystal violet lactone, 3,3-(bis-aminophenyl)-phthalide, 3-(aminophenyl-3-indolyl)-phthalide, or 2,6-diamino-fluoranes, in order to produce blue, navy blue, grey or black colours.

Surprisingly, the colour formers of formulae (1) to (4) used in the thermoreactive recording material of the present invention are characterised by a high rate of colour development with acid developers and at the same time by excellent light fastness. The recording material normally comprises at least a carrier, a colour former, an electron acceptor substance and optionally a binder. Thermoreactive recording systems comprise for example heat-sensitive recording and copying materials and papers. These systems are used, for example, for recording information, e.g. in electronic computers, teleprinters or telewriters, and in measuring instruments. The image (mark) formation can also be effected manually with a heated pen. Laser beams can also be used to produce heat-induced marks. The thermoreactive recording material can be so composed that the colour former is dispersed or dissolved in one binder layer and the developer is dissolved or dispersed in the binder in a second layer. A second possibility consists in dispersing both the colour former and the developer in the binder in one layer. By means of heat the binder is softened at specific areas and the colour former comes into contact with the electron acceptor substance at those points at which heat is applied and the desired colour develops at once.

The developers are the same electron-accepting substances as are used in pressure-sensitive papers.

Examples of such products are attapulgite clay, silton clay, silica, bentonite, halloysite, aluminium oxide, aluminium sulphate, aluminium phosphate, zinc chloride, kaolin or any acid clay, or an acid polymeric material, for example a phenolic polymer, an alkylphenolacetylene resin, a maleic acid/rosin resin or a partially or completely hydrolysed polymer of maleic acid and styrene, ethylene, vinyl methyl ether or carboxypolymethylene, or phenolic compounds, for example 4-tert. butylphenol, 4-phenylphenol, 4-hydroxydiphenyl oxide, α-naphthol, β-naphthol, 4-hydroxybenzoic acid methyl ester, 4-hydroxyacetophenone, 2,2′-dihydroxydiphenyl, 4,4-isopropylidene-diphenol, 4,4′-isopropylidene-bis-(2-methylphenol), 4,4′-bis-(hydroxyphenyl)valeric acid, hydroquinone, pyrogallol, phloroglucinol, p-, m- and o-hydroxybenzoic acid, gallic acid, 1-hydroxy-2-naphthoic acid, as well as boric acid and aliphatic dicarboxylic acids, e.g. tartaric acid, oxalic acid, maleic acid, citric acid, citraconic acid or succinic acid. Preferably, mixtures of two or more of these substances are also used as developer.

Fusible, film-forming binders are preferably used for the manufacture of the thermoreactive recording material. These binders are normally water-soluble, whereas the colour formers and the developers are insoluble in water. The binder should be able to disperse and fix the colour former and the developer at room temperature. By applying heat the binder softens or melts, so that the colour former comes in contact with the developer and a colour is able to form. Examples of binders which are soluble or at least swellable in water are hydrophilic polymers, for example polyvinyl alcohol, polyacrylic acid, hydroxyethyl cellulose, methyl cellulose, carboxymethyl cellulose, polyacrylic amide, polyvinyl pyrrolidone, gelatin and starch.

If the colour former and the developer are in two separate layers, it is possible to use water-insoluble binders, i.e. binders which are soluble in non-polar or only weakly polar solvents, for example natural rubber, synthetic rubber, chlorinated rubber, alkyd resins, polystyrene, styrene/butadiene copolymers, polymethylmethacrylates, ethyl cellulose, nitrocellulose and polyvinyl carbazole. The preferred arrangement, however, is that in which the colour former and the developer are contained in one layer in a water-soluble binder.

The thermoreactive coatings can contain further additives. The coatings can contain, for example, talc, $TiO_2$, ZnO or $CaCO_3$ or also organic pigments, for example urea/formaldehyde polymers for improving the degree of whiteness, facilitating the printing of papers, and for preventing the heated pen from sticking. In order to effect the colour formation only within a limited temperature range, it is possible to add substances such as urea, thiourea, acetanilide, phthalic anhydride or other appropriate fusible products which induce the simultaneous melting of the colour former and developer.

Typical thermoreactive recording materials in which the colour formers are used, are described, for example, in German Offenlegungsschriften 2,110,854 and 2,228,581, in French Pat. No. 1,524,826 and in Swiss Pat. Nos. 164,976, 407,184, 444,196 and 444,197.

The following manufacturing Directions and Examples will serve to illustrate the invention. Unless otherwise indicated, the percentages are by weight.

MANUFACTURING DIRECTIONS

A. 2.7 g of bis-(4-dimethylaminophenyl)-carbinol and 1.59 g of 1-ethyl-2-methylindole are stirred at reflux temperature for 5 hours in 50 ml of methanol. After cooling to 20° C the precipitated reaction product is filtered off, washed with 30 ml of methanol and dried at 60° C, to yield 3.82 g of a colour former of formula (11)

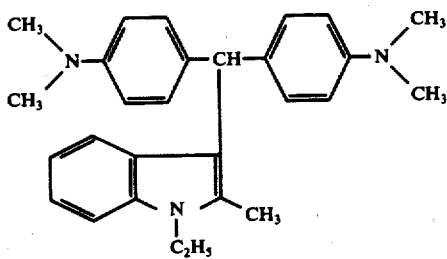

which melts at 159°–160° C.

B. The colour formers of formulae (12) to (18) listed in the following table are obtained by repeating the procedure of Manufacturing Direction A and replacing 1-ethyl-2-methylindole by equimolar amounts of 1-phenyl-3-methyl-5-pyrazolone, 1-phenyl-3-methyl-5-amino-pyrazole, 1-methyl-4-hydroxy-2-quinolone, 5,5-dimethyl-1,3-dioxo-cyclohexane, acetyl acetone, acetoacetic anilide or malonic dinitrile. The last column of the tables indicates the shades, with absorption maxima, which the colour formers develop when brought into contact with silton clay.

Table $$\left[\begin{array}{c} R \\ \diagdown \\ N\text{—}\phantom{a}\!\!\!\bigcirc\!\!\!\!\phantom{a}\text{—} \\ \diagup \\ R \end{array}\right]_2 CH\text{—}Z_3$$

| for- mula | R | R | $Z_3$ | melting point | silton clay colour | $\lambda_1$ | $\lambda_2$ |
|---|---|---|---|---|---|---|---|
| 11 | CH₃ | CH₃ | 1-ethyl-2-methylindol-3-yl | 159–160 | violet | 614 | 575 |
| 12 | CH₃ | CH₃ | 1,3-dimethyl-5-oxo-2-phenyl-pyrazolin-4-yl | 192–193 | blue | 616 | 580 |
| 13 | CH₃ | CH₃ | 5-amino-1,3-dimethyl-2-phenyl-pyrazol-4-yl | 146–147 | blue | | |
| 14 | CH₃ | CH₃ | 4-hydroxy-1,3-dimethyl-2-oxo-1,2-dihydroquinolin-yl | 198–200 | blue | 616 | 573 |
| 15 | CH₃ | CH₃ | 2,5,5-trimethyl-3,6-dioxocyclohexyl | 170–174 | blue | 616 | 575 |
| 16 | CH₃ | CH₃ | —CH(COCH₃)₂ | 142–144 | blue | 616 | 573 |
| 17 | CH₃ | CH₃ | —CH(CO—CH₃)—CONH—C₆H₅ | 201–202 | blue | 616 | 578 |
| 18 | CH₃ | CH₃ | —CH(CN)₂ | 167–169 | blue | 616 | 576 |

EXAMPLE 1

MANUFACTURE OF A THERMOREACTIVE PAPER 6 g of an aqueous dispersion which contains 1.57% of the colour former of formula (11) obtained in Manufacturing Direction A and 6.7% of polyvinyl alcohol are mixed with 134 g of an aqueous dispersion which contains 14% of 4,4-isopropylidene-diphenyol and 6% of polyvinyl alcohol. This mixture is applied to a paper and dried. Contacting the paper with a heated ball-point pen produces a vivid violet colour of excellent lightfastness. Similar results are obtained by using any of the other colour formers of formulae (12) to (18).

Particularly good results are obtained by also mixing in silton or attapulgite clay in addition to 4,4-isopropylidene-diphenol.

EXAMPLE 2 a. 7 g of the colour former of formula (12), 300 g of a 10% aqueous polyvinyl alcohol solution and 130 ml of water are triturated together until an aqueous preparation with a viscosity of 23 to 28 centipoise is obtained. The diameter of the colour former particles is approximately 1 to 3 μ.

b. At the same time, 70 g of 4,4'-isopropylidene-diphenol and 300 g of a 10% aqueous polyvinyl alcohol solution are triturated with 130 ml of water for 1 hour. After trituration, the particles still have a diameter of 1 to 3 μ.

c. 6 g of colour former dispersion and 134 g of the phenol dispersion are then mixed and applied to a paper sheet to give a coating of 3 to 4.5 g/m². The dried paper is coated with 3% of colour former, 67% of developer and 30% of polyvinyl alcohol. When the surface of this paper is contacted with a heated pen, blue markings are immediately formed.

Instead of the above colour former, it is also possible to use with success the colour formers of formulae (11) and (13) to (18) of the table.

We claim

1. A heat sensitive recording material containing at least one color former and at least one electron acceptor in at least one binder layer on paper, said color former having the formula

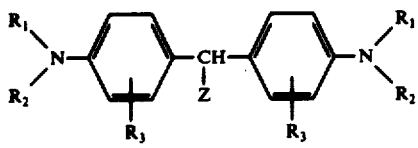
(1)

wherein $R_1$ and $R_2$, which can be the same or different, represent hydrogen, alkyl of at most 12 carbon atoms which is unsubstituted or substituted by cyano or halogen, alkoxyalkyl of 2 to 8 carbon atoms, benzyl or phenyl, $R_3$ represents hydrogen, halogen, nitro, alkyl of 1 to 4 carbon atoms or alkoxy of 1 to 4 carbon atoms, and Z represents alkenyl of at most 12 carbon atoms, unsubstituted or ring-substituted aralkyl or aralkenyl, or represents the radical of a reactive organic methylene compound or of a heterocyclic compound which does not contain active methylene groups.

2. A recording material according to claim 1 which contains at least one colour former of the general formula (1), wherein Z represents the radical of an aliphatic, cycloaliphatic or heterocyclic compound which contains an active methylene group.

3. A recording material according to claim 2 which contains at least one colour former of the general formula (1), wherein Z represents the radical

in which X represents an electrophilic group and Y represents an inert organic group or an electrophilic group.

4. A recording material according to claim 2 which contains at least one colour former of the general formula (1), wherein Z represents the radical of a reactive ketomethylene compound.

5. A recording material according to claim 4 which contains at least one colour former of the general formula (1), wherein Z represents a 1-aryl-5-pyrazolon-4-yl radical which is substituted in 3-position by alkyl of 1 to 4 carbon atoms.

6. A recording material according to claim 5 which contains at least one colour former of the formula (1), wherein Z represents a 1-aryl-3-methyl-5-pyrazolon-4-yl radical.

7. A recording material according to claim 1 which contains at least one colour former of the general formula (1), wherein Z represents a 3-indolyl radical which is unsubstituted or substituted by halogen, cyano, nitro, alkyl of 1 to 8 carbon atoms, alkoxy of 1 to 4 carbon atoms, acyl of 2 to 4 carbon atoms, benzyl or phenyl.

8. A recording material according to claim 7 which contains at least one colour former of the general formula (1), wherein Z represents a 1-($C_1$-$C_8$-alkyl)-2-methyl-3-indolyl or 1-benzyl-2-methyl-3-indolyl radical.

9. A recording material according to claim 1 which contains at least one colour former of the general formula

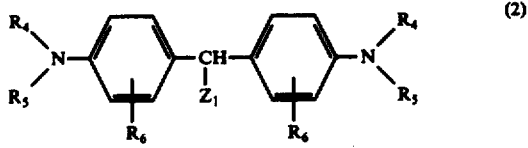
(2)

wherein each of $R_4$ and $R_5$ independently represents hydrogen, alkyl of 1 to 4 carbon atoms or benzyl, $R_6$ represents hydrogen, methyl, methoxy or chlorine, and $Z_1$ represents an indolyl radical which is unsubstituted or substituted by alkyl of 1 to 8 carbon atoms, alkoxy of 1 to 4 carbon atoms, alkanoyl of 2 to 4 carbon atoms, benzyl or phenyl, a 5-amino-pyrazole radical or represents the radical of an open or cyclic ketomethylene compound.

10. A recording material according to claim 9 which contains at least one colour former of the general formula

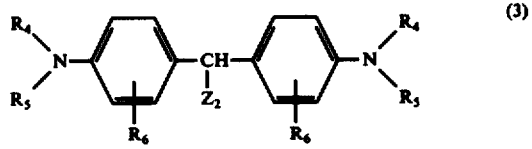
(3)

wherein $R_4$, $R_5$ and $R_6$ are as defined in claim 9 in respect of formula (2), and $Z_2$ represents 1-($C_1$-$C_8$-alkyl)-2-methyl-3-indolyl, 1-benzyl-2-methyl-3-indolyl, 1-aryl-3-methyl-5-pyrazolon-4-yl, 1-aryl-3-methyl-5-amino-pyrazol4-yl or represents the radical of an open or cyclic 1,3-diketone or of an acylacetic anilide which is bound through the methylene group.

11. A recording material according to claim 10, wherein as a radical of an open 1,3-diketone or of an acylacetic anilide which is bound through the methylene group $Z_2$ represents a radical of formula (3:1)

wherein each of $X_1$ and $Y_1$ independently represents acyl of 2 to 8 carbon atoms or the group of formula

(3.2)

wherein the benzene ring A is unsubstituted or substituted by methyl, methoxy, halogen or nitro.

12. A recording material according to claim 10, wherein as radical of a cyclic 1,3-diketone $Z_2$ represents a 5,5-di-$C_1$-$C_4$-alkyl-1,3-dioxo-cyclohexyl radical or a 1-$C_1$-$C_4$-alkyl-4-hydroxy-2-quinolonyl radical or the radical of a 6-hydroxy-3-cyano- or carbonamido-4-$C_1$-$C_4$-alkyl-2-pyridone which in 1-position is unsubstituted or substituted by alkyl of 1 to 4 carbon atoms.

13. A recording material according to claim 10, wherein the colour former is of formula (3), wherein both $R_4$ and $R_5$ represent methyl or ethyl, $R_6$ represents hydrogen and $Z_2$ represents 1-methyl-2-methyl-indol-3-yl, 1-ethyl-2-methyl-indol-3-yl, 1-benzyl-2-methyl-indol-3-yl, 1-phenyl-3-methyl-5-pyrazolon-4-yl, 1-chlorophenyl-3-methyl-5-pyrazolon-4-yl, 1-phenyl-3-methyl-5-amino-pyrazol-4-yl, acetyl-acetonyl, 5,5-dimethyl-1,3-dioxo-cyclohex-2-yl, 1-methyl-4-hydroxy-2-quinolon-3-yl or represents the radical of an acetoacetic anilide of formula

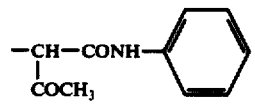

14. A heat-sensitive recording material according to claim 1 which contains attapulgite clay, silton clay, acid phenolic compounds, acid phenolic resins or a solid organic acid as electron acceptor.

* * * * *